United States Patent [19]

Kinoshita

[11] Patent Number: 4,660,798
[45] Date of Patent: Apr. 28, 1987

[54] HANDPIECE SUPPORT ARRANGEMENT

[75] Inventor: Tsuyoshi Kinoshita, Nagasaki, Japan

[73] Assignee: Mitsubishi Denki Kabushiki Kaisha, Tokyo, Japan

[21] Appl. No.: 759,675

[22] Filed: Jul. 29, 1985

[30] Foreign Application Priority Data

Jul. 30, 1984 [JP] Japan .............................. 59-115051[U]

[51] Int. Cl.⁴ .............................................. F16M 3/00
[52] U.S. Cl. ................................... 248/648; 248/123.1
[58] Field of Search .................. 248/648, 162.1, 123.1, 248/292.1, 297.1, 331

[56] References Cited

U.S. PATENT DOCUMENTS

| 660,868 | 10/1900 | Reid | 248/162.1 |
| 3,194,531 | 7/1965 | Langer | 248/162.1 X |
| 3,481,340 | 12/1969 | McKnight et al. | |
| 3,749,342 | 7/1973 | Perrine | 248/123.1 |

FOREIGN PATENT DOCUMENTS 55-26859 7/1980 Japan .
0216814 12/1983 Japan .................................... 248/648

Primary Examiner—Ramon O. Ramirez
Attorney, Agent, or Firm—Leydig, Voit & Mayer

[57] ABSTRACT

A support arrangement for supporting a handpiece comprises a main body, a support post having one end secured to the main body, a movable arm movably mounted on the other end of the support post for supporting the handpiece, a counter-weight mounted on the other end of the movable arm adjacent the support post with an axis intersecting a horizontal axis of the movable arm and parallel to an axis of the support post for maintaining the movable arm substantially horizontal when the movable arm is not in operation. The support post extends obliquely upwards from the main body so as to shorten the length of the movable arm for better maneuverability.

7 Claims, 4 Drawing Figures

HANDPIECE SUPPORT ARRANGEMENT

BACKGROUND OF THE INVENTION

This invention relates to a support apparatus, and more particularly to a support apparatus for supporting a handpiece for laser surgery.

The construction of a conventional supporting device for supporting a handpiece 5 is shown in FIG. 1. In the drawing, a $CO_2$ laser oscillator and control instrument thereof are enclosed in a box-shaped main body 1. A support post 2 is vertically supported by the main body 1 so as to extend upwards. A movable arm 3 comprising a vertical portion 3a and a horizontal portion 3b connected by a universal joint 6 is pivotably supported by the end 8 of the support post 2. A handpiece 5 is pivotably supported by the end of the vertical portion 3a of the arm 3 which is remote from the joint 6. At the other end of the arm 3 is mounted a counterweight 4 which enables the horizontal portion 3b of the arm 3 to maintain a horizontal attitude when the handpiece 5 is not in operation. A surgical operating table 7 is also illustrated in the drawing.

Next, the operation of this device will be explained. The movable arm 3 is pivoted about the center of the end 8 of the support post 2, which is bent at the joint 6, and is moved to a desired position of the operating table 7 by an operator (not shown). When the unillustrated $CO_2$ laser oscillator is turned on, a laser beam generated by the laser oscillator passes through the support post 2 and the arm 3, and is emitted from the hand piece 5 and is used for surgery.

However, in the conventional support device, the horizontal portion 3b of the movable arm 3 must be quite long for it to extend to any portion of an operating table 7. Therefore, the movable arm 3 is subjected to a large shear force and large bending moment at the center of the end 8 due to its own weight. Therefore, the mechanical strength of the movable arm 3 must be increased to keep the arm 3 straight, which requires that the movable arm 3 be of sturdier construction with thicker walls. However, this increases the weight of the movable arm 3 and makes the handpiece 5 difficult to maneuver.

SUMMARY OF THE INVENTION

An object of this invention is to provide a support arrangement in which the above defects of the prior art eliminated.

Another object of this invention is to provide a support arrangement in which the horizontal length of the movable arm can be shortened.

Still another object of the present invention is to provide a support arrangement which offers a superior maneuverability of a supported handpiece.

PREFERRED EMBODIMENT OF THE INVENTION

Figure 1:
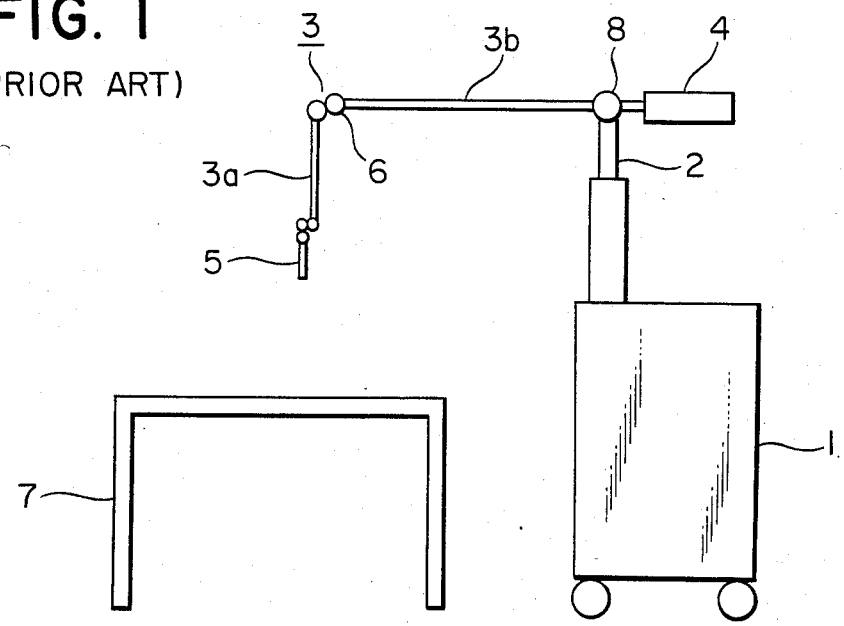
FIG. 1 is a schematic side view of a conventional support arragement used for a laser operation.

Hereinafter, an embodiment of a supporting device will be explained with reference to FIGS. 2 and 3. The same reference numerals as in FIG. 1 refer to the same or corresponding portions, and therefore an explanation of those portions will be omitted.

A box-shaped main body 11 comprising a laser oscillating unit (not shown) is rotatably supported by a wheeled bogie 10. An upwardly obliquely extending support post 12 is mounted on the upper portion thereof. Referring to FIG. 3, the support post 12 extends obliquely at an angle $\alpha$ which is preferably 45 degrees from the vertical. A movable arm 13 comprising a vertical portion 13a and a horizontal portion 13b which are rotatably connected with each other by a universal joint 6 is rotatably supported about a horizontal axis by the upper end 8 of the support post 12. A counterweight 4 for maintaining the horizontal portion 13b of the movable arm 13 in a horizontal attitude is mounted on the end of the arm 13 opposite the handpiece 5 adjacent the support post 12 and is oriented so that its axis intersects the horizontal first axis and is parallel to the axis of the support post 12. The handpiece 5 from which a laser beam is emitted is mounted on the other end of the movable arm. As the conventional support apparatus was constructed above, if the distance from the main body 11 to the handpiece 5 is the same as that of the above mentioned-device, the following holds true:

Length of $3b$ = Length of $13b + 12h$ or in other words
Length of $13b$ = Length of $3b - 12h$ where $12h$ is the length of a horizontal projection of the support post 12.

Accordingly, this invention enables the horizontal portion 13b of the arm 13 to be shorter by an amount $12h$ than the horizontal portion 3b of the conventional device. Thus, in this invention, the effective length of the moment arm of the movable arm 13, measured from the end 8, can be shortened by reducing the weight of the movable arm 13 itself. The bending moment and the shear force acting on the arm 13 can be reduced to a small value. Thus, the arm 13 will not bend due to is own weight. Therefore, the laser beam which is generated by the laser oscillating unit in the main body 11 can pass through the support post 12 and the arm 13 without contacting the inner walls thereof. As both the bending moment and shear force acting on the arm 13 are smaller, the thickness of the arm, can be decreased, and the handpiece 5 can be smoothly operated. As the counterweight 4 is parallel with the support post 12, it does not disturb the operation of another instrument.

Figure 2:
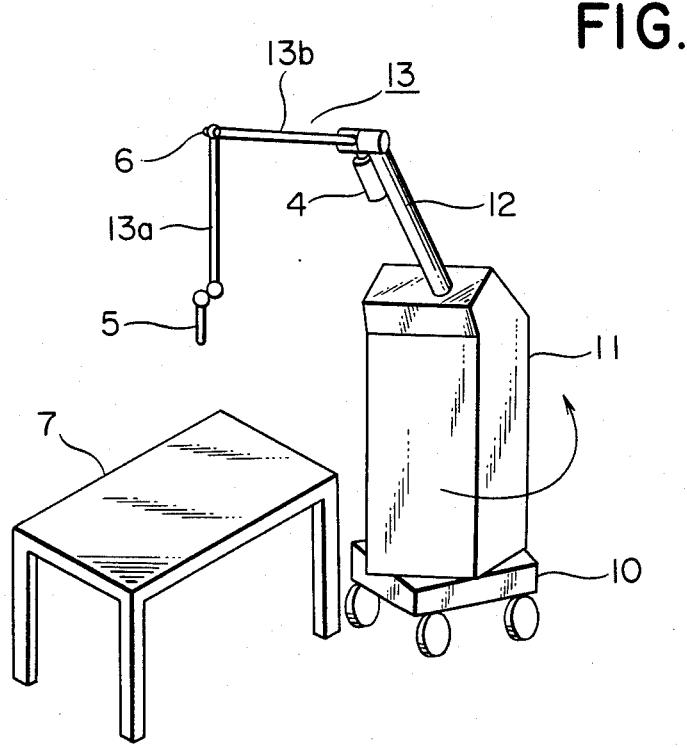
FIG. 2 is a schematic perspective view of an embodiment of this invention.
Figure 3:
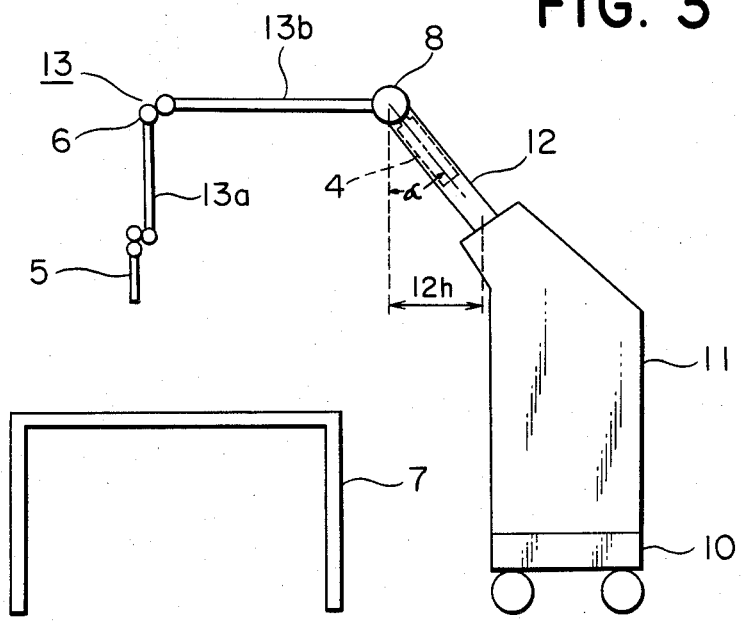
FIG. 3 is a side view of the embodiment of FIG. 2.
Figure 4:
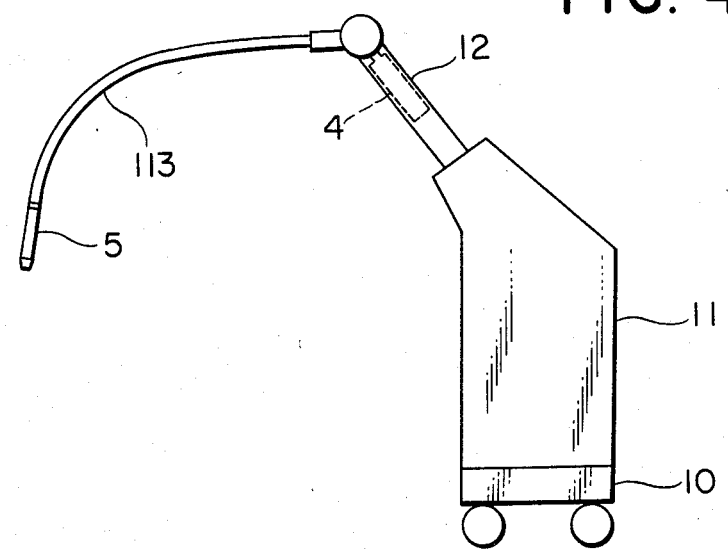
FIG. 4 is a side view of a further embodiment in which the arm comprises an optical fiber.

In this embodiment, the main body 11 is supported by a bogie 10, but it is also possible for the main body 11 to be constructed so as to freely rotate on the bogie as shown in FIG. 2. With such a structure the handpiece 5 can be more precisely placed in a desired position.

Alternatively, it is possible to use a movable arm 113 made of an optical fiber. If so, the weight of the arm can be decreased and a reflecting mirror for an optical path is not needed.

Furthermore, each of the above-mentioned embodiments is of support devices for a laser surgical device. However, the present invention is not limited to use as part of a laser surgical device and can be used as a support device for a light, a drawing instrument, or other item.

What is claimed is:

1. A support arrangement for movably supporting a handpiece comprising:
    a main body;
    a support post mounted at one end to said main body, said support post extending axially upwardly obliquely from the vertical so that the horizontal projection of the length of said support post extends toward the handpiece;
    a movable arm pivotally mounted on the other end of said support post for movement about a horizontal first axis for supporting the handpiece; and
    a counterweight disposed on said movable arm for maintaining said movable arm in a substantially horizontal position, said counterweight being mounted adjacent said support post at the intersection of the axes of said support post and said movable arm with an axis of said counterweight intersecting said horizontal first axis and parallel to the axis of the support post when said movable arm is in a substantially horizontal position.

2. A support arrangement as claimed in claim 1 wherein said main body comprises a laser oscillating unit, and said support post and said movable arm include a path for conducting a laser beam from said laser oscillating unit to the handpiece.

3. A support arrangement as claimed in claim 1 wherein said movable arm comprises a plurality of joints.

4. A support arrangement as claimed in claim 1 wherein said counterweight is an elongated member extending parallel to and adjacent said support post when said movable arm is in the horizontal position.

5. A support arrangement as claimed in claim 1 wherein said support post is tilted at about 45 degrees from the vertical.

6. A support arrangement as claimed in claim 1 wherein said movable arm includes an optical fiber.

7. A support arrangement as claimed in claim 2 wherein said laser unit comprises a $Co_2$ laser unit.

* * * * *